United States Patent
Menzi et al.

(10) Patent No.: US 7,731,687 B2
(45) Date of Patent: *Jun. 8, 2010

(54) SAFETY SPRING CATHETER INTRODUCER ASSEMBLY

(75) Inventors: Thomas Menzi, Felsberg (DE); Kevin Woehr, Felsberg (DE); Juergen Fuchs, Bad Emstal (DE)

(73) Assignee: B. Braun Melsungen AG, Melsungen (DE)

( * ) Notice: Subject to any disclaimer, the term of this patent is extended or adjusted under 35 U.S.C. 154(b) by 89 days.

This patent is subject to a terminal disclaimer.

(21) Appl. No.: 12/018,741

(22) Filed: Jan. 23, 2008

(65) Prior Publication Data

US 2008/0147003 A1 Jun. 19, 2008

Related U.S. Application Data

(60) Continuation of application No. 11/490,602, filed on Jul. 20, 2006, now Pat. No. 7,374,554, which is a division of application No. 10/109,797, filed on Mar. 29, 2002, now Pat. No. 7,500,965.

(30) Foreign Application Priority Data

Apr. 18, 2001 (DE) .......................... 201 06 697 U1

(51) Int. Cl.
*A61M 5/00* (2006.01)
*A61M 5/178* (2006.01)
*A61M 5/32* (2006.01)

(52) U.S. Cl. .................. 604/110; 604/198; 604/164.08

(58) Field of Classification Search ................. 604/110, 604/263, 192, 198, 164.01, 164.07, 164.08
See application file for complete search history.

(56) References Cited

U.S. PATENT DOCUMENTS

| | | | | |
|---|---|---|---|---|
| 5,601,536 A | * | 2/1997 | Crawford et al. | 604/263 |
| 6,117,108 A | * | 9/2000 | Woehr et al. | 604/110 |
| 6,749,588 B1 | * | 6/2004 | Howell et al. | 604/164.08 |
| 7,374,554 B2 | * | 5/2008 | Menzi et al. | 604/110 |
| 7,500,965 B2 | * | 3/2009 | Menzi et al. | 604/198 |

FOREIGN PATENT DOCUMENTS

WO   WO 99/52584   10/1999

OTHER PUBLICATIONS

Notice of Rejection dated Apr. 2, 2008 from corresponding Japanese Application No. 2002-113276 (2 pages).

* cited by examiner

*Primary Examiner*—Kevin C Sirmons
*Assistant Examiner*—Andrew M Gilbert
(74) *Attorney, Agent, or Firm*—Klein, O'Neill & Singh, LLP

(57) ABSTRACT

A catheter introducer assembly is disclosed whereby the safety spring clip moves into position to block the needle tip occurs as a direct consequence of the withdrawal of the needle from the catheter bore. The catheter introducer assembly according to the present invention comprises a needle and a needle hub, a catheter and a catheter hub, and a safety spring clip assembly. The safety spring clip assembly being designed to permit the needle to slide inside the spring clip assembly until the needle stop located on the needle meets the proximal wall to thereby prevent further movement of the safety spring clip. A method of using the catheter introducer assembly according to the present invention is also provided.

20 Claims, 7 Drawing Sheets

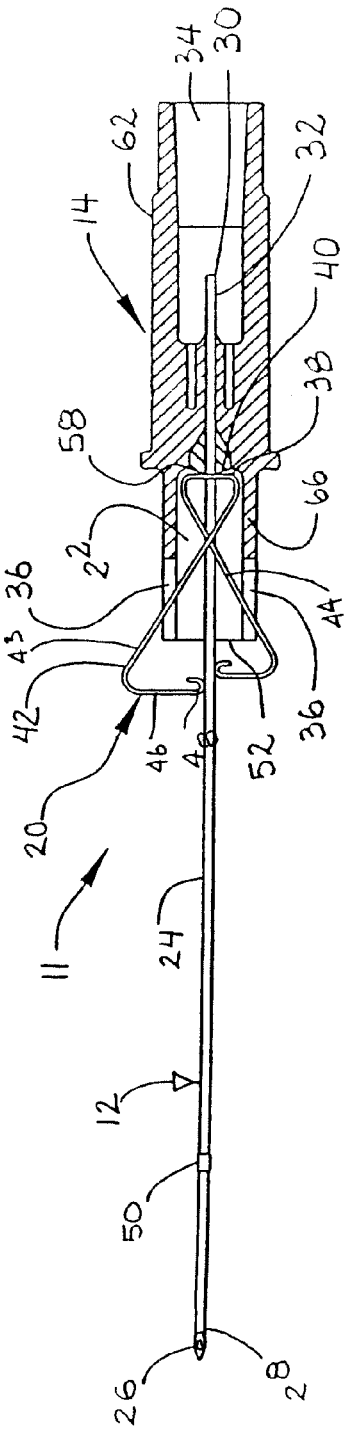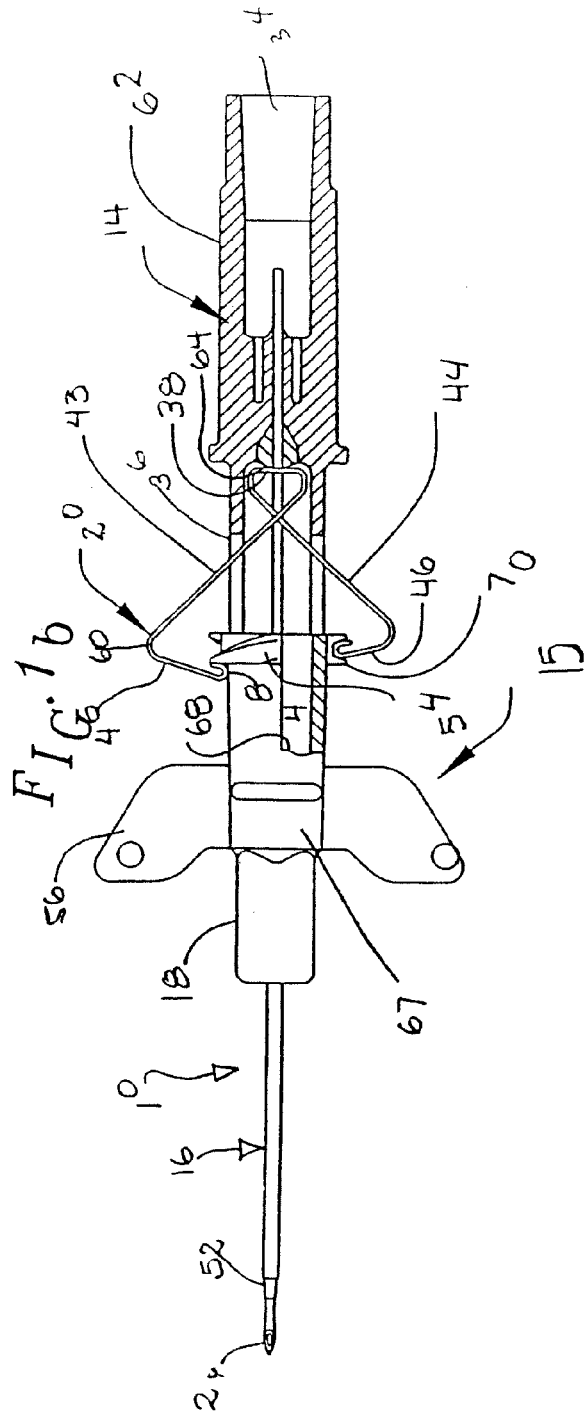

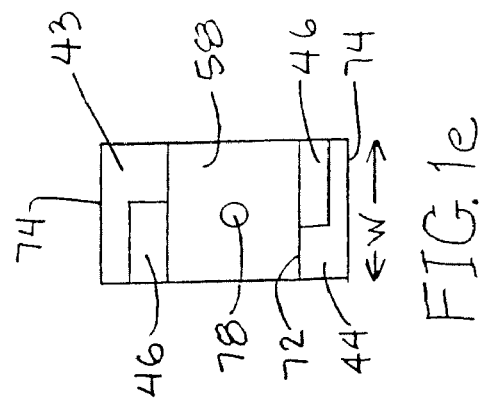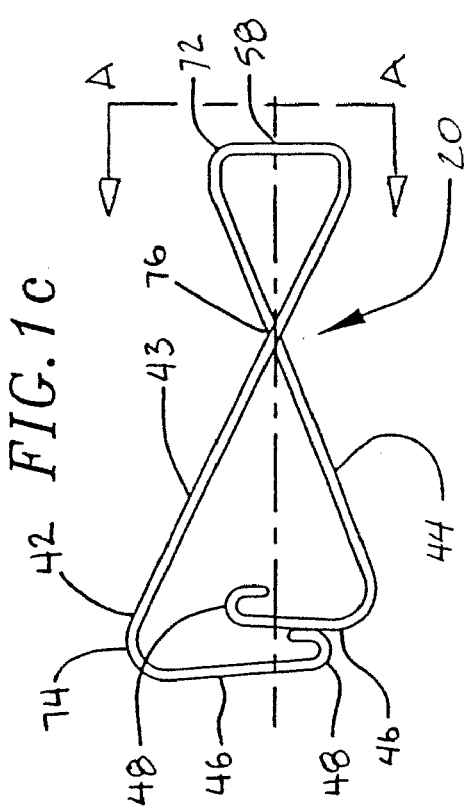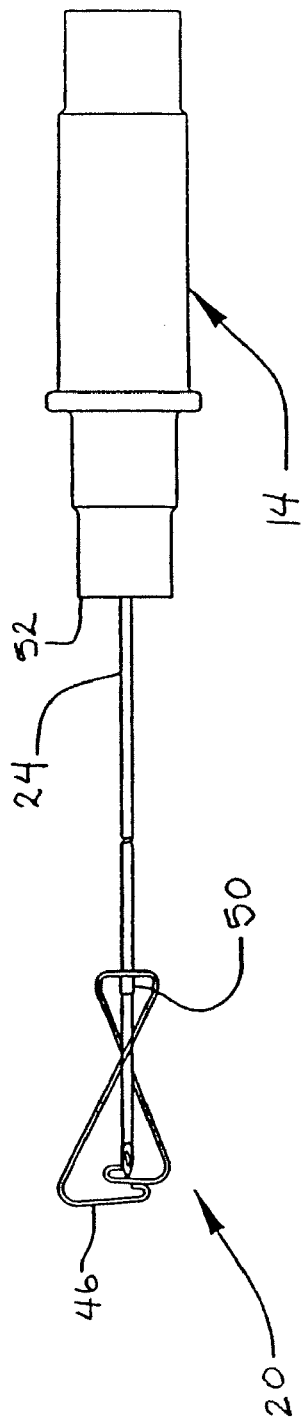

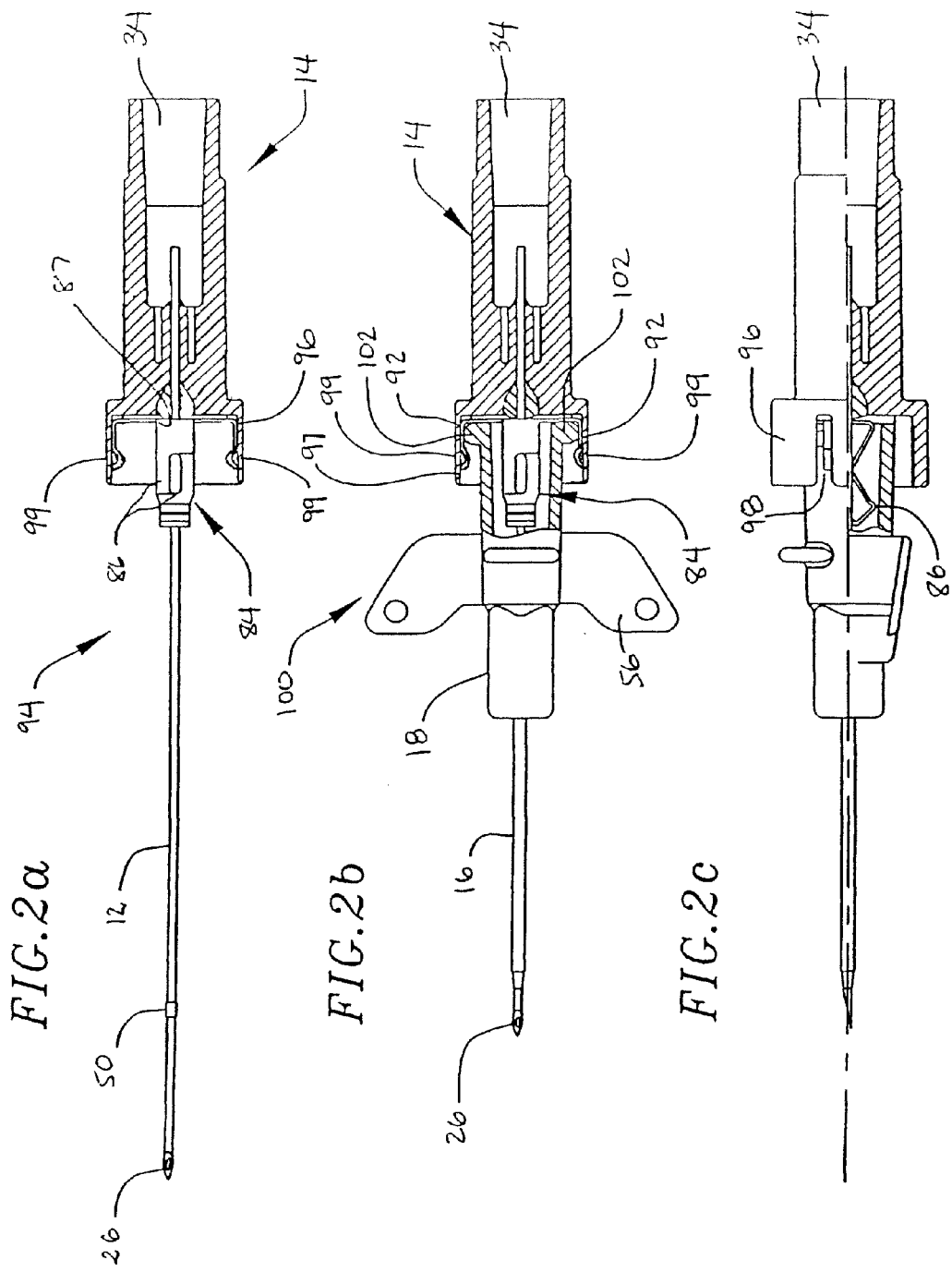

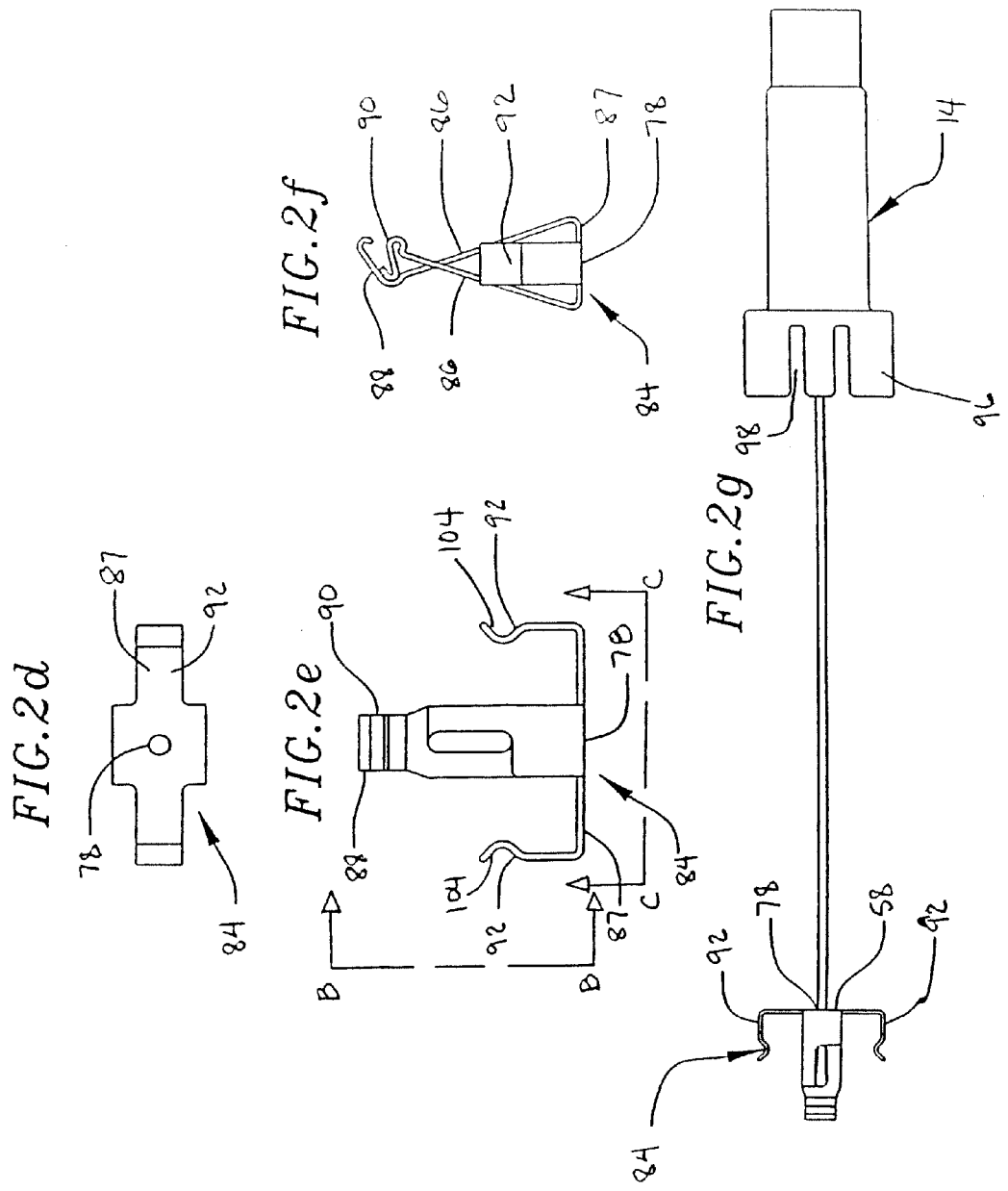

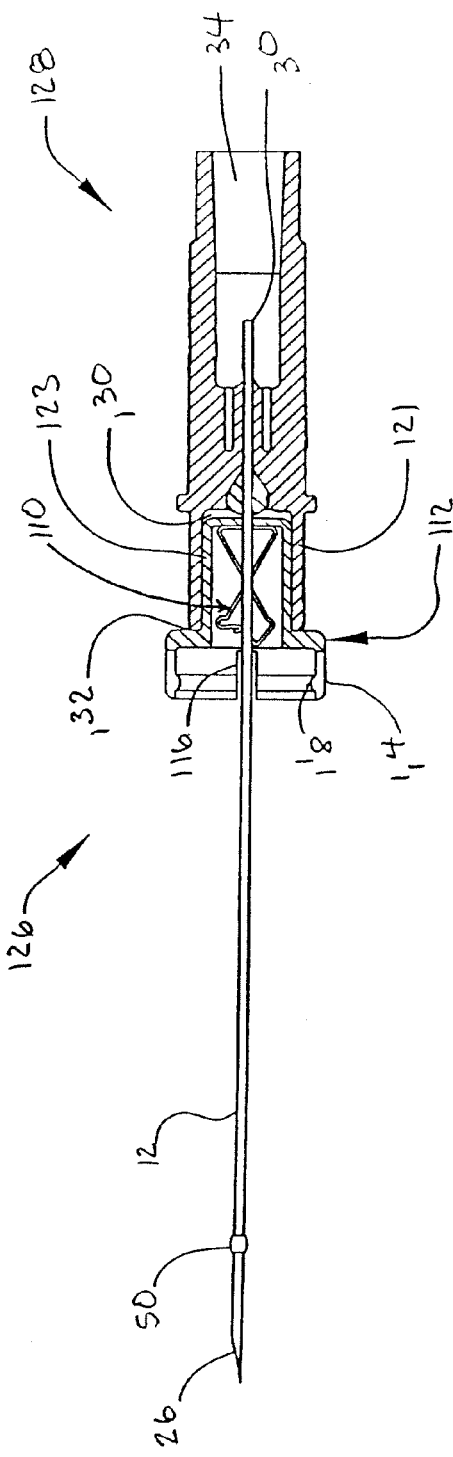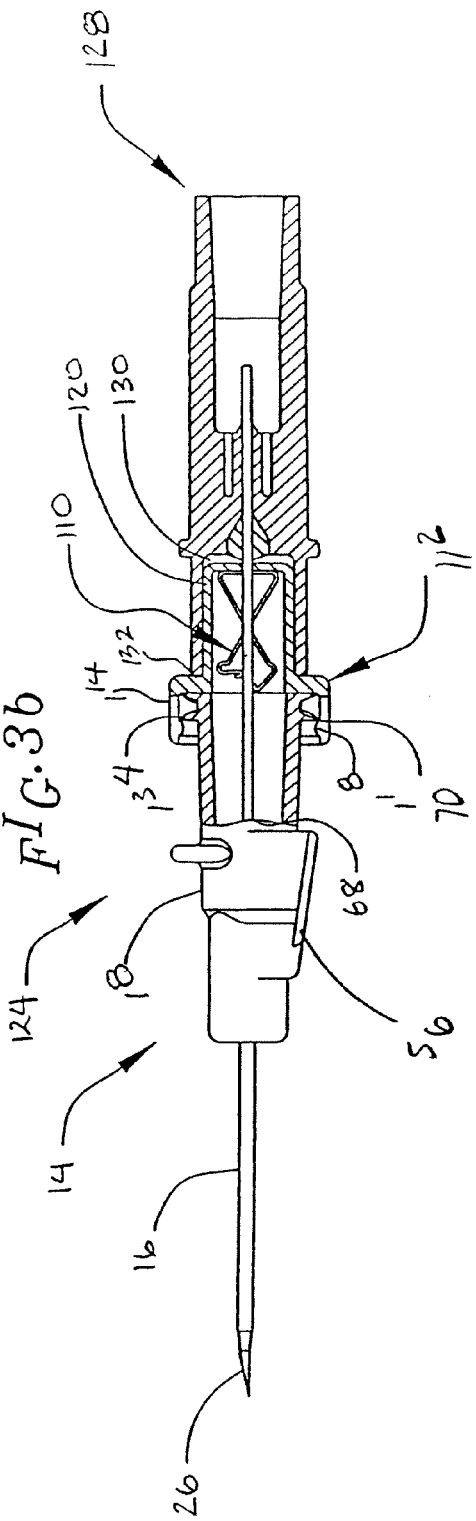

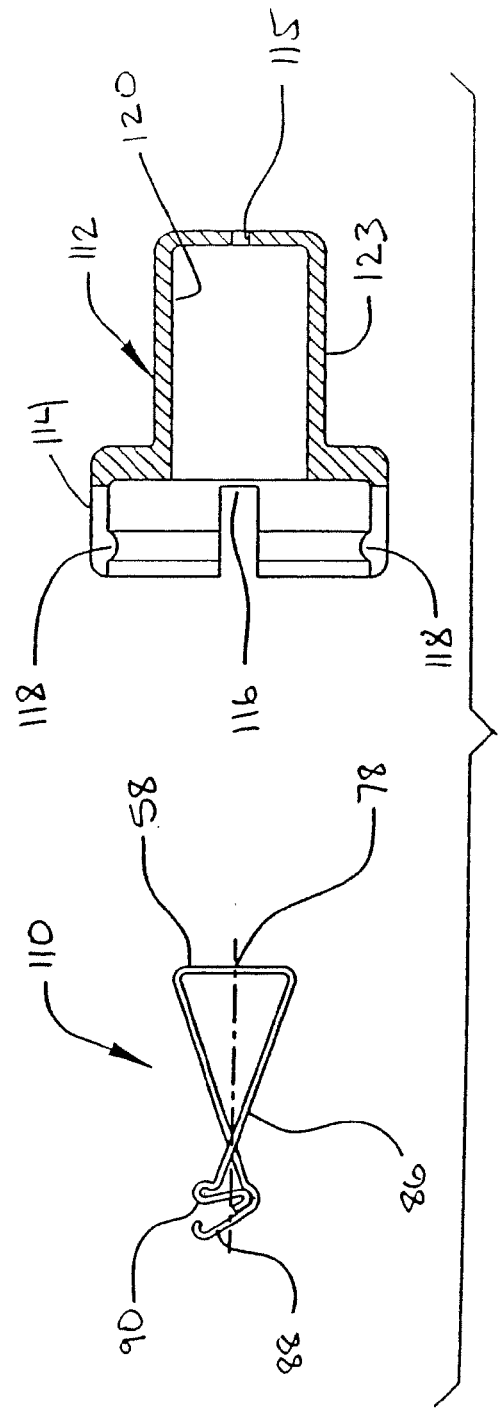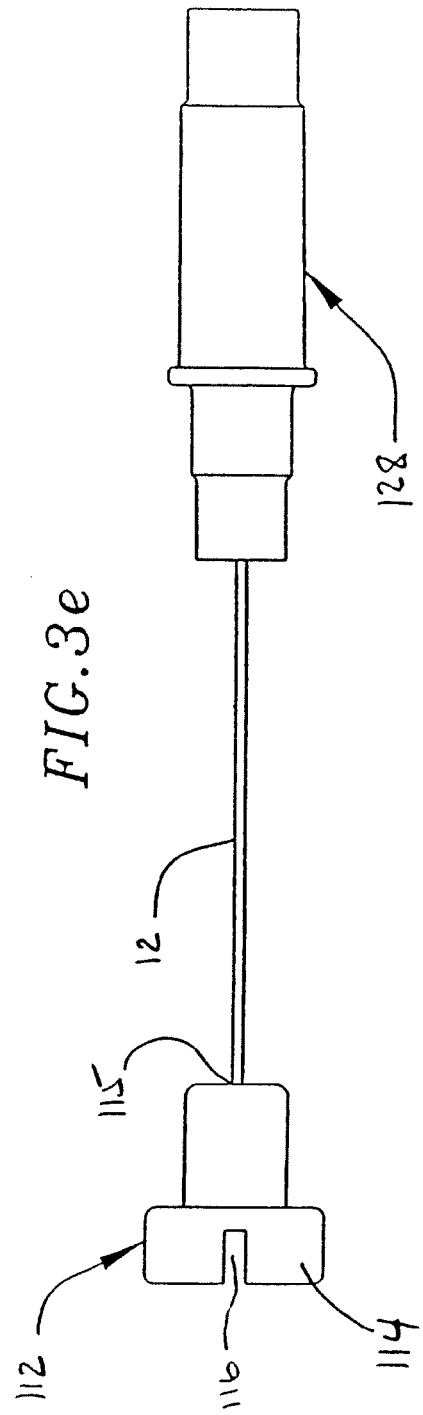

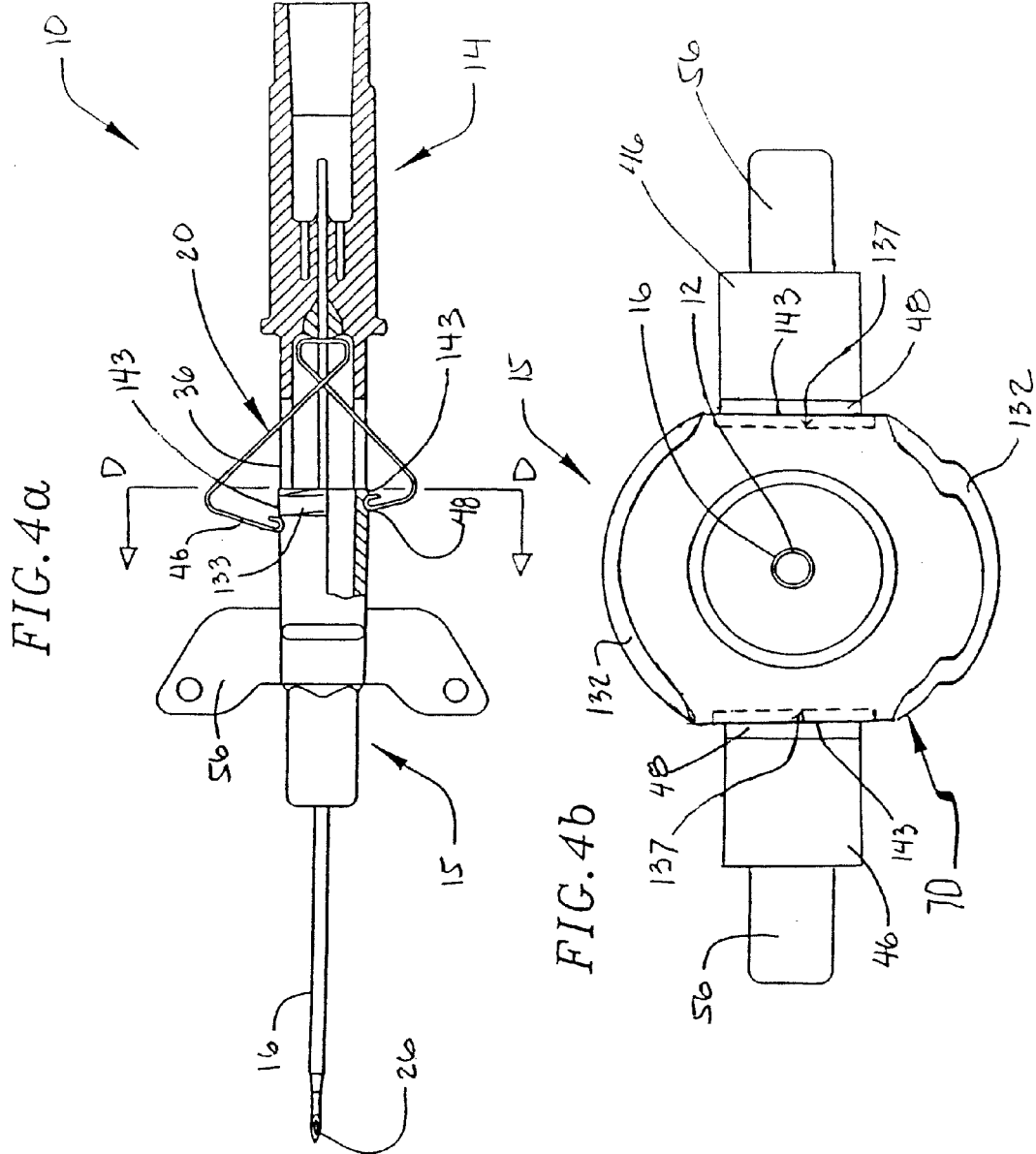

SAFETY SPRING CATHETER INTRODUCER ASSEMBLY

CROSS-REFERENCE TO RELATED APPLICATION

This is a Continuation of Ser. No. 11/490,602, now U.S. Pat. No. 7,374,554, filed Jul. 20, 2006, which is a Divisional Application of Ser. No. 10/109,797, now U.S. Pat. No. 7,500,965, filed Mar. 29, 2002, which claims priority to German Patent Application No. 201 06 697 U1, filed Apr. 18, 2001. The contents of each of these references are expressly incorporated herein by reference.

Safety IV catheters discussed herein generally relate to catheters with safety features and specifically to safety IV catheters with blocking mechanisms for automatically blocking the needle tips as the tips are withdrawn from the catheters to thereby facilitate the safe handling of catheter needles.

BACKGROUND

Medical care of individuals requires the widespread use of catheter devices for taking blood samples, for intravenous (IV) drug delivery, and for the introduction or removal of other fluids. The use of a catheter device (hereinafter, "catheter") typically involves first inserting a needle and plastic catheter combination into the vein of a patient and then removing the needle to leave only the plastic catheter in the vein. The withdrawn needle is then typically disposed of.

To assist in the disposal process and to help prevent health care workers from becoming injured when coming in contact with an exposed tip of a used needle, needle guards have been developed to block the tip of a needle after it has been withdrawn. Indeed, with potentially fatal infectious diseases, such as Acquired Immune Deficiency Syndrome (AIDS) and hepatitis which can be transmitted through the exchange of body fluids by accidental contact with the needle tip of a used needle, needle stick protection has never been more important.

Commercially available safety catheter devices generally may be grouped into three basic categories: (1) those which include an activation mechanism to hide the withdrawn needle within a needle shield; (2) those which require placement of a separate needle guard; and (3) those which include a sliding shield which must be manually positioned distally over the used needle. Despite their laudable intentions, most of these safety catheter devices suffer from some shortcomings. Among other things, some require an extra step beyond the normal insertion and withdrawal steps and/or require additional complicated pieces to ensure that the needle guard and the catheter remain attached during the withdrawal procedure.

Of the first category, there are several different conventional systems available with a common design which utilizes a frictionally locked spring biased needle shield to automatically engage the needle tip when the needle is withdrawn from the catheter. While these devices may be considered adequate, a user can unknowingly apply sufficient force during the withdrawal process to overcome the frictional engagement in the device so that the spring biased shield can slip off of the distal end of the needle and leave the needle tip exposed.

Another example of the first category prior art spring biased needle shield utilizes a slightly expanded portion of the needle tip (such as a protrusion or a crimped surface) to prevent the needle shield from sliding off of the distal end of the needle once the shield has engaged. In many of these designs, the needle shield is first frictionally positioned in the catheter body before use or insertion into a patient's vein. However, after insertion and during the withdrawal process, the frictionally positioned shield has a tendency to disengage from the catheter body before complete separation of the needle from the catheter. When this occurs, the needle tip is left exposed due to the early separation of the spring shield.

In conventional prior art devices of the second and third categories, there are a number of different designs which include needle shields with either a spring-clip fitting or a frictional fitting. A needle shield of this type is either placed directly on the needle tip or is movable from the base of the needle to the tip of the needle along the longitudinal direction of the needle. In the latter embodiment, a user can manually slide the needle shield towards the needle tip to engage the needle shield thereto. However, these manually activated designs require that the user either slide or apply the needle shield to the tip of the needle by hand, thus significantly raising the risk of unintentional contact with the needle tip.

In another prior art catheter assembly, the safety guard is configured to sit in the catheter hub until the needle is withdrawn. Once the needle is withdrawn, the safety guard automatically unlocks from the catheter hub to block the needle tip. This design, however, adds an inherent adverse drag between the needle and the safety guard as the needle is withdrawn. This drag is undesirable because it can create an uneven withdrawal movement.

Accordingly, there remains a need for a catheter assembly which reduces the risk of early disengagement by both holding the needle shield and the catheter body together during the withdrawal process and simultaneously and automatically disengaging from the catheter body with substantially zero adverse drag and blocking the needle tip once the withdrawal process is complete.

SUMMARY

According to the present invention, there is provided a catheter introducer assembly design that automatically moves the needle spring clip into position to block the needle tip upon detachment of the needle from the catheter body. This action occurs as a direct consequence of the withdrawal of the needle from the catheter bore, without the need for the activation of any additional mechanism to complete the needle withdrawal process.

The catheter introducer assembly according to the present invention comprises a needle and a needle hub, a catheter and a catheter hub and a safety spring clip assembly. The needle has an elongated shaft which defines a longitudinal axis. The needle also includes a needle tip and has a proximal end secured to the needle hub by conventional means. The needle further comprises a distal end which is proximate the needle tip and has a needle stop located between the proximal and distal ends. The needle stop serves as a limiting feature to limit the movement of the safety spring clip when the safety spring clip comes in contact therewith. The catheter is fixedly attached to the catheter hub by conventional means and is slideably mounted over a substantial portion of the needle.

The safety spring clip assembly comprises a needle blocking mechanism for blocking the needle tip and a restraining mechanism for preventing the safety spring clip from separating from the needle. The safety spring clip is slideably mounted onto the needle and generally sits between the catheter hub and the needle hub and, in an exemplary embodiment, is removably secured to both hubs. The safety spring clip is configured to slideably ride the needle shaft and has a sliding range that is limited on one side by the needle stop and on the other side by the needle hub.

In an exemplary embodiment, the safety catheter introducer unit comprises a catheter hub having an internal passage and a catheter mounted thereto, the catheter hub further having a proximal end and an external surface. Another component is a needle hub which has a needle hub distal end and a needle hub proximal end, and a needle defining a longitudinal axis and having a needle distal end, a needle proximal end. The needle also has a needle shaft, a needle tip at the needle distal end and a needle opening at the needle proximal end. The further having a needle stop positioned proximate to the needle tip, the needle stop having at least one portion extending out of the longitudinal axis of the needle. The needle hub is arranged such that the needle extends out of the distal end of the needle hub and into the catheter. The needle clip interacts with the other components as follows: the needle clip is disposed about the needle and having a first portion between the proximal end of the catheter hub and the distal end of the needle hub and having a second portion that either engages the external surface of the proximal end of the catheter hub or the needle shaft, the needle tip safety guard further having a needle opening therein through which the needle is in sliding communication. The needle opening is configured to engage the needle stop and prevent the needle clip from completely separating from the needle. However, when the second portion engages the needle shaft, the safety catheter assembly should be practiced with the needle hub further comprising a shroud.

The invention also includes a method for utilizing the catheter introducer. The method comprising utilizing the catheter introducer assembly as described above to first position and introduce the needle and catheter into a patient and then to withdraw the needle from the catheter while automatically blocking the withdrawn needle tip from accidental contact therewith.

BRIEF DESCRIPTION OF THE DRAWINGS

These and other features and advantages of the present invention will become appreciated as the same becomes better understood with reference to the specification, claims and appended drawings wherein:

FIG. 1a is a semi-schematic cross-sectional top view of a needle assembly provided according to the principles of this invention;

FIG. 1b is a semi-schematic cross-sectional top view of a catheter introducer assembly in a ready position provided according to the principles of this invention;

FIG. 1c is a semi-schematic top view of a needle safety clip provided according to the principles of this invention;

FIG. 1d is a semi-schematic top view of an activated safety clip provided according to the principles of this invention;

FIG. 1e is a semi-schematic end view of the safety clip taken at line A-A of FIG. 1c;

FIG. 2a is a semi-schematic cross-sectional top view of an alternative needle assembly provided according to the principles of this invention;

FIG. 2b is a semi-schematic cross-sectional top view of an alternative catheter introducer assembly in a ready position provided according to the principles of this invention;

FIG. 2c is a semi-schematic cross-sectional side view of the catheter introducer assembly shown in FIG. 2b;

FIG. 2d is a semi-schematic end view of the needle safety clip taken along line C-C of FIG. 2e;

FIG. 2e is a semi-schematic top view of a needle safety clip provided according to the principles of this invention;

FIG. 2f is a semi-schematic side view of the needle safety clip taken along line B-B of FIG. 2e;

FIG. 2g is a semi-schematic top view of an activated safety clip provided according to the principles of this invention;

FIG. 3a is a semi-schematic cross-sectional side view of another alternative needle assembly provided according to the principles of this invention;

FIG. 3b is a semi-schematic cross-sectional side view of another catheter introducer assembly in a ready position provided according to the principles of this invention;

FIG. 3c is a semi-schematic side view of a needle safety clip used in the embodiment of FIGS. 3a and 3b;

FIG. 3d is a semi-schematic cross-sectional side view of a removable shroud provided according to the principles of this invention;

FIG. 3e is a semi-schematic side view of an activated safety clip provided according to the principles of this invention;

FIG. 4a is a semi-schematic cross-sectional top view of another alternative catheter introducer assembly provided according to the principles of this invention; and FIG. 4b is a semi-schematic cross-sectional end view of a catheter taken along line D-D of FIG. 4a.

DETAILED DESCRIPTION

The detailed description set forth below in connection with the appended drawings is intended as a description of the presently preferred embodiments of the safety catheter introducer assembly provided in accordance with the present invention and is not intended to represent the only forms in which the present invention may be constructed or utilized. The description sets forth the features and the steps for constructing and using the safety catheter introducer assembly of the present invention in connection with the illustrated embodiments. It is to be understood, however, that the same or equivalent functions and structures may be accomplished by different embodiments that are also intended to be encompassed within the spirit and scope of the invention. Also, as denoted elsewhere herein, like element numbers are intended to indicate like or similar elements or features.

Referring now to FIGS. 1a and 1b, there is shown and described an exemplary catheter introducer assembly in accordance with practice of the present invention, which is generally designated 10 (FIG. 1b). The catheter introducer assembly 10 shown therein comprises a needle assembly 11 (FIG. 1a), which includes an introducing needle 12 mounted to a needle hub 14 in a conventional manner, and a catheter body 15 (FIG. 1b), which includes a flexible tubular catheter 16 mounted to a plastic catheter hub 18 also in a conventional manner (FIG. 1b). The catheter introducer assembly 10 further comprises a safety spring clip or a needle clip 20 which is slideably mounted to the needle 12 and removably secured within the needle hub 14 at the holding chamber or bore 22 in the distal end of the needle hub 14.

The needle 12 further comprises a needle shaft 24, a needle tip 26 at the needle distal end 28 and a needle inlet 30 at the needle proximal end 32, which, in an exemplary embodiment, extends into a flash chamber 34 in the proximal end of the needle hub 14. In an exemplary embodiment, the needle hub 14 further comprises a pair of diametrically opposed lateral slits 36 located distally at the holding bore 22. The lateral slits 36 permit access for a pair of spring arms to extend out from the holding bore 22 to removably engage the catheter hub, as further discussed below. Thus, the needle clip can be thought of as having a first portion or proximal end which sits within the bore 22 and a second portion or distal end which extends out from the bore to engage the catheter hub 18.

The catheter introducer assembly has three positions, a pre-ready position (FIG. 1a), a ready position (FIG. 1b), and a withdrawal or fully retracted position (FIG. 1d). In the pre-ready position, the safety spring clip 20 sits within the holding bore 22 with its proximal end 38 in contact with the holding bore proximal end 40. However, it is understood that the stated contact is not required, and, alternatively, instead of just resting within the holding bore 22, the safety spring clip 20 can slightly frictionally engage the inside diameter of the holding bore 22. As further discussed below, this slight frictional engagement, if employed, should require less force to disengage than the force necessary to separate the safety spring clip 20 from the catheter hub 18. This way, the spring clip 20 will disengage from the needle hub 14 as the needle is withdrawn from the patient before the spring clip 20 disengages from the catheter hub 18. In the pre-ready position, the safety spring clip 20, which comprises a distal end 42, two elongated spring arms 43, 44, two distal end walls 46, and a spring lip 48 on each of the distal end walls or spring fingers 46, is biased in a first position and touches the needle shaft 24 with its two spring lips 48.

The needle 12 further comprises a needle stop 50 (which is also commonly referred to as a crimp, a protrusion, or a bulge; herein collectively referred to as a "needle stop") disposed along the length of the needle 12 between the proximal 32 and the distal 28 ends, and preferably proximate to the distal end 28 of the needle 12. In an exemplary embodiment, the needle stop 50 has a contour that is different than the contour of the needle 12, which has a uniform outside diameter along the entire shaft 24. The needle stop 50 can comprise a crimped portion formed by crimping the needle with known crimping methods. At the crimped portion 50, the needle shaft's diameter is therefore different from the uniform outside diameter. Thus, according to one embodiment, the needle stop 50 has a shape that extends from the uniform outside shaft diameter. In other words, the needle stop has a shape or a dimension that is larger than the uniform outside diameter. As further discussed below, this larger dimension allows the needle stop 50 to engage an aperture or opening in the proximal end of the safety spring clip 20 and to prevent the spring clip 20 from further moving along the shaft 24.

In the ready position (FIG. 1b), a substantial portion of the needle 12 including the needle stop 50 sits within the bore of the catheter hub 16 but with the needle tip 26 projecting past the distal tip 52 or opening of the catheter 16. As shown and as further discussed below, the needle safety clip 20 is in contact with both the needle hub 14 and the catheter hub 18. Specifically, the safety clip proximal end 38 is positioned within the holding bore 22 while its spring arms 43, 44 extend through the lateral slits 36 to releasably engage the exterior surface of the catheter hub proximal end 54 with the spring lips 48.

A number of needle hub designs can be utilized in the present invention provided that the needle 12 and the needle tip guard 20 can be held together and the catheter hub 18 can be adjoined thereto. In the exemplary embodiment shown in FIGS. 1a and 1b, the needle hub 14 comprises an integrally molded body 62, which as previously discussed, defines an axial cylindrical inner needle passageway or flash chamber 34. The holding bore 22 is coaxial with the flash chamber 34 and has a support wall 64 at the proximal end 40 of the holding bore 22. The spring wall 58 of the safety spring clip 20 is positioned within the holding bore 22 and against the support wall 64.

The holding bore 20 can have any suitable design provided that the needle tip guard 20 can be positioned therein. In the embodiment shown in FIGS. 1a and 1b, for example, the needle hub 14 has an enclosing wall 66 which defines the holding bore 22 therein. The holding bore 22 has a diameter that is sufficiently larger than the largest dimension of the safety clip proximal end 38 so that the proximal end can be removed therefrom with minimum resistance.

In an exemplary embodiment of the catheter introducer assembly 10 provided in accordance with practice of the present invention, the structure is configured to facilitate manipulation of the needle hub 14 between the thumb and finger(s). For example, the needle hub 14 enclosing wall 66 may include a stepped portion or a textured surface to provide better gripping. The needle hub body 62 can be made of a transparent material, such as, for example, a transparent plastic, so that when the needle is successfully inserted into a patient's vein, back flash of blood can be observed running through the needle and into the flash chamber 34.

Any catheter hub 18 design can be utilized in the present invention provided that the catheter 16 is held therein, the needle 12 is allowed to pass therethrough, and the safety spring clip 20 can be adjoined therewith. Turning again to FIG. 1b, in an exemplary embodiment, the catheter hub 18 comprises an integrally molded body 67 which defines an axial cylindrical inner catheter passageway 68 having dimensions designed to accept and fixedly attach the catheter 16 therein. Conventional Luer fitting threads 70 can be formed on the proximal end 54 to serve as a connection point for IV supply lines and the like once the catheter insertion process is complete. As further discussed below, the Luer fitting 70 also functions as an anchoring point for the spring lips 48 when the catheter assembly is in the ready position. As best shown in FIG. 1b, when assembled, the exterior surface of the catheter hub 18 at the Luer fitting 70 is engaged by the spring fingers 46 of the spring clip 20, and more specifically is removably gripped by the spring lips 48 of the spring clip 20.

Referring now to FIG. 1c, there is shown and described an exemplary embodiment of a safety spring clip 20 provided in accordance with practice of the present invention. The safety spring clip 20 can be made from a resilient metal such as stainless steel and, as previously discussed, comprises two elongated spring arms 43, 44 formed by bending the resilient material to form a first set of two hinges 72. The safety spring clip 20 is also bent at the distal end 42 to form a second set of two hinges 74. Assuming that the width of the spring clip is the transverse measurement of the safety spring clip 20 shown in FIG. 1e, the width of the upper spring arm 43 and width of the lower spring arm 44 from a position just proximal to the cross-over point 76 to a position just proximal of the second set of two hinges 74 is less than half of the width of the spring 20 when measured at the spring wall 58. Preferably the width of the spring arms 43, 44 is such that there is a space between arms at the cross-over point 76 to enable the needle 12 to pass therebetween. Note, although the lower spring arm 44 is shown to be shorter than the upper spring arm 43, the reverse arrangement can also provide a functional alternative. The safety spring clip 20 has a relaxed or unbiased position when it is in the position indicated in FIG. 1c. It is understood that the spring clip 20 is slideably mounted over the needle 12 before the creation of the needle stop 50 or before the needle is attached to the needle hub 14.

Referring now to FIG. 1e, there is shown an end elevation view of the safety spring clip 20 taken at line A-A of FIG. 1c. As shown, the safety spring clip comprises a circular aperture 78 centrally located at the spring wall 58. The aperture 78 has a diameter that is slightly larger than the uniform diameter of the needle 12, but is less than the largest measured width of the needle stop 50. Thus, as shown in FIG. 1d, the spring end wall 58 is capable of sliding about the needle shaft 24 from between the needle stop 50 to the needle hub distal end 52.

However, the end wall 58 is prevented from moving distally past the needle stop 50 because the diameter of the aperture 78 is smaller than the width of the needle stop.

In an alternative embodiment, the aperture 78 of the spring clip 20 can have an oval, a star or other suitable shape. Additionally, spring clips provided in accordance with the present invention can have a single arm. If a single spring arm is used, such as either spring arm 43 or 44, a sufficient spring force must be incorporated thereto so that as the needle 12 is being withdrawn, the spring clip 20 does not disengage from the catheter hub 18 before the separation of the needle spring clip 20 and the holding bore 22.

In addition to the features incorporated into the catheter hub described above, many other optional features can be provided. For example, the catheter hub may optionally comprise a handle and guidance means for guiding the needle 12 and the catheter 16 inside the patient. The catheter hub 18 may also comprise a plug optionally fitted into the proximal end of the hub for guiding the needle 12 within the catheter 16 and catheter hub 18, or alignment means to ensure that the catheter hub and the needle hub are oriented in a certain direction when assembled. A vent filter may also be fitted into the end of either the catheter hub 18 or the needle hub 14. Additionally, any electronics suitable for using the catheter to measure or send signals to and/or from the patient may also be incorporated into the catheter hub 18.

The catheter introducer assembly 10 operates by inserting the catheter introducer assembly in its ready position into a vein of a patient and then withdrawing the needle 12 while leaving the catheter 16 inserted in the vein. In an exemplary embodiment, the withdrawal of the inserted needle is performed by firmly gripping the catheter hub 18, such as by gripping a pair of wings 56 located thereon, and preventing the catheter hub from moving while at the same time gripping the needle at the needle hub 14 and then withdrawing the needle 12 by pulling or sliding the needle hub 14 proximally to separate the needle from the catheter.

As the needle 12 is proximally withdrawn from the catheter 16, the needle clip 20 disengages from the holding bore 22. As the needle 12 is further proximally withdrawn, the needle clip proximal end 38 slides relative to the needle shaft 24 until it contacts the needle stop 50. More specifically, the aperture or opening 78 located at the spring wall 58 slides relative to the uniform outer diameter of the shaft 24 until the opening 78 contacts the needle stop 50. As previously discussed, the opening 78 is smaller in dimension than the needle stop 50. Therefore, at this point, the needle clip 20 is prevented from further sliding distally relative to the needle shaft 24 by the engagement of the needle stop 50 with the opening 78. Essentially anchored by the needle stop 50, any additional pulling or application of withdrawal force causes the needle clip 20 to deflect about the elongated spring arms 43, 44 and the front hinges 60, which causes the spring lips 48 to ride over the Luer fitting 70 at the proximal end 54 of the catheter hub 18. Finally, as the needle 12 is withdrawn past the proximal end of the catheter hub and the spring lips 48 are pulled past the Luer fitting, the spring arms 43, 44 resiliently snap together into their first or relaxed position to thereby cause the transverse walls 46 to close over and block the needle tip 26 (FIG. 1*d*). In this blocked position, a user or an administrator is guarded against accidentally contacting the needle tip.

Although the needle stop 50 comprising a crimp is preferred due to its simple and inexpensive nature, the needle stop can be formed with any shape suitable to prevent the needle 12 from being completely dislodged from the needle clip 20. In alternative embodiments, the needle stop 50 can be formed by other techniques rather than by crimping, for example, by electroetching material above and below the needle stop area to reduce the diameter of the remainder of the needle 12 or by grinding the needle 12 to a desired configuration. Either technique provides the needle 12 with an integral construction, which is preferred. Other possible techniques include plating the area selected for enlargement, insert molding a band of polymeric material around the needle 12 or by welding a band of metal around the needle.

Referring to FIGS. 2*a*, 2*b*, 2*e*, and 2*f*, there is shown an alternative embodiment of the catheter introducer assembly of the present invention. The needle tip guard 84 or safety spring clip of this embodiment comprises elongated spring arms 86 which extend distally from the needle tip guard end wall 87. Turning particularly to FIGS. 2*e* and 2*f*, at the ends of the spring arms 86 are two inwardly extending transverse wall portions or spring fingers 88, 90. The transverse wall portions 88, 90 have generally L-shaped ends and project inwardly toward the longitudinal axis of the needle 12. In this embodiment, as best shown in FIGS. 2*d*, 2*e*, 2*f*, and 2*g* the safety spring clip 84 further comprises a pair of holding arms 92, which, as is further discussed below, are designed to contact both the shroud 96 (located on the needle hub 14) and the catheter hub 18 (FIG. 2*b*). The spring fingers 88, 90 and the spring arms 86 are in a relaxed or unbiased position as shown in FIG. 2*f*.

The end wall 87 of the safety spring clip 84 has a restraining opening or an aperture 78 disposed therein for the same limiting function as previously discussed for the embodiment described with respect to FIGS. 1*a*-1*e*. The opening 78 is sized to allow the needle shaft to slidingly move therethrough and engages the needle stop 50 to stop the spring clip from being pulled distally off of the tip of the needle 12. The spring clip 84 of this embodiment is configured so that when the needle tip 26 moves proximally of the spring fingers 88, 90, the spring arms 86 spring closed to allow the spring fingers 88, 90 to move together to block the needle tip 26.

Referring to FIG. 2*a*, the needle assembly 94 comprises a needle hub 14 and a needle 12 disposed therein. The needle assembly 94 further comprises a modified section that includes the shroud 96 which has a plurality of lateral slits 98 formed therein. However, the number of lateral slits 98 may be reduced or eliminated all together.

The catheter body assembly 100 (FIG. 2*b*) includes a pair of projections 102 which are Luer flanges or lugs which act as anchor points and which are located at the proximal end of the catheter hub 18. Like the Luer threads 70 of the FIG. 1*b* embodiment, the projections 102 interact with the safety spring clip 84 to removably secure the catheter hub 18 to the needle hub 14 in the ready position. More specifically, the projections 102 interact with the engaging portions 104 (FIG. 2*e*) located on the holding arms 92 to removably secure the catheter hub 18 to the needle hub 14 in the ready position (FIG. 2*b*). The projections 102 can also connect with conventional connectors such as an IV fitting and the like.

An alignment groove (not shown) may be provided in the shroud 96 to guide the safety spring clip 84 into the shroud 86 so that the needle clip engaging portions 104 (FIG. 2*e*) match up with the projections 102. Alternatively, the projections 102 may be provided as a ring formed around the exterior surface of the catheter hub at its proximal end. If so, an alignment groove may be omitted because no matter in what orientation the safety spring clip 84 is inserted, the engaging portions 104 will be aligned with the ring.

Like the embodiment discussed in FIGS. 1*a*-1*d*, the present embodiment has a pre-ready position (FIG. 2*a*), a ready position (FIGS. 2*b* and 2*c*), and a fully retracted position (FIG. 2*g*). The catheter introducer assembly of FIGS. 2*a*-2*g* operates by first inserting the needle tip 26 and the catheter 16 in the ready position (FIGS. 2b and 2c) into a patient's vein and then withdrawing the needle 12 while leaving the catheter 16 inserted in the vein. As the needle 12 is withdrawn from the patient, the holding arms 92 on the spring clip move distally with respect to the shroud 96.

As the needle 12 is further withdrawn from the catheter 16, the safety spring clip 84, which still releasably engages the catheter hub projections 102, slides distally with respect to the needle shaft 32 until the needle stop 50 engages the opening 78 in the spring end wall 87. The safety spring clip 84 is prevented from further movement toward the needle tip due to the engagement between the opening 78 and the needle stop 50. As the needle is pulled further in the proximal direction, the additional pulling force causes the spring clip 84 to begin separating from the catheter hub 18.

At this point, the holding arms 92 deflect outwardly as they are pulled passed the projections 102 located on the proximal end of the catheter hub 18. Finally, as the needle 12 is fully retracted from the catheter hub 18, the holding arms 92 completely disengage from the projections 102, and the needle tip 26 is drawn distally past the spring fingers 88, 90, the spring arms 86 spring closed into their relaxed position and the spring fingers move together to block the needle tip. This results in the needle tip being blocked by the spring clip 84 as shown in FIG. 2g.

Another alternative embodiment of the catheter introducer assembly provided in accordance with the practice of the present invention is shown in FIGS. 3a-3e. This embodiment includes a shroud 112 that is removably secured to the needle hub and that travels along the needle shaft with the safety spring clip as the spring clip blocks the needle tip. As is shown separately in FIGS. 3c and 3d, the safety spring clip 110 is similar to the safety spring clip 84 of FIGS. 2d-2f but does not include the holding arms 92. The safety spring clip 110 comprises a restraining opening 78 (FIG. 3c), a spring wall 58, a pair of spring arms 86, and a pair of spring clip transverse wall portions or spring fingers 88, 90. The removable shroud 112 comprises a covering portion 114, which preferably includes at least a pair of lateral slits 116, a restraining element 118 for engaging the catheter hub 18, an annular bore 120 for removably receiving the needle spring clip 110, and a restraining opening or aperture 115 (FIG. 3d) for receiving and traveling over the needle shaft. The restraining element 118 resembles protrusions formed along the internal circumference of the covering portion 114 that are bisected by lateral slits 116.

Turning now to FIGS. 3a, 3b, and 3e, there is shown and described the catheter introducer assembly 124 in a pre-ready position (FIG. 3a), a ready position (FIG. 3b), and a fully withdrawn or retracted position (FIG. 3e). In the pre-ready position (FIG. 3a), the needle assembly 126 comprises a needle hub 128 that is similar to the needle hub of FIG. 1a. Accordingly, the needle hub 128 has a flash chamber 34 and receives a needle 12 in a similar fashion as previously discussed. However, the holding bore 130 has been modified to receive a removable shroud 112 and does not include lateral slits, although lateral slits may be included if desired. The removable shroud 112 can be made, for example by injection molding, from thermoplastic polymer such as polypropylene.

The holding bore 130 and the shroud 112 are configured to only slightly frictionally engage. That is, when the needle hub 128 is withdrawn from the catheter, the holding bore 130 and the shroud 112 are configured to disengage from each other before the shroud 112 separates from the catheter hub 18. In an exemplary embodiment, the removable shroud 112 and the distal end of the needle hub 128 contacts the proximal side of the covering portion 114 at a contact point 132 (FIG. 3a).

However, instead of having the contact point 132, in an alternative embodiment, there may be a slight separation between the distal end of the needle hub and the proximal side of the covering portion. Also, although not shown, the removable shroud 112 may include a pin formed to the inside of the covering portion 114 to interact with a slot (not shown) on the catheter hub. The pin and the slot can interact to align the catheter hub with the shroud 112 as the catheter hub 18 is being received by the shroud 112. The catheter hub 14 is essentially the same as previously discussed with respect to the embodiment illustrated in FIG. 1b. Accordingly, the catheter hub 14 comprises a flexible catheter 16, a Luer fitting or threads 70, and a pair of wings 56.

The catheter introducer assembly 124 operates by inserting the catheter introducer assembly in its ready position into a patient's vein and then withdrawing the needle 12 while leaving the catheter 16 inserted in the vein. In an exemplary embodiment, the withdrawal of the inserted needle is performed by firmly gripping the catheter hub 14 and preventing the catheter hub from moving while at the same time gripping the needle hub 128 and then withdrawing the needle by pulling or sliding the needle hub proximally to separate the needle from the catheter.

As the needle 12 is withdrawn, the removable shroud 112 separates from the holding bore 130. This separation is ensured by configuring the frictional engagement between the removable shroud 112 and the holding bore 130 to require less force to separate than the removal force between the restraining element 118 and the Luer fitting 70 at contact point 134 (FIG. 3b). In short, the friction between the inside surface 121 of the holding bore 130 (FIG. 3a) and the outside surface 123 of the shroud 112 should be less than the gripping force between the restraining element 118 and the Luer fitting 70.

As the needle 12 is further withdrawn from the catheter 16, both the removable shroud 112 and the safety clip 110 move relative to the needle shaft until the needle stop 50 comes into contact with the hole or aperture 78 in the spring wall 58. The contact with the needle stop 50 prevents the removable shroud 112 and the safety spring clip 110 from further movement toward the needle tip of the needle. With the restricted movement, further pulling force causes the removable shroud 112 to separate from the Luer fitting 70. This separation is assisted by the lateral slits 116 in the covering portion 114, which allows the covering portion 114 to deflect outward as the restraining element 118 travels over the Luer fitting 70.

Finally, as the needle tip 26 is withdrawn past the proximal end of the catheter hub 14 and proximal of the pair of spring fingers 88, 90, the spring arms 86 resiliently release and spring closed into their relaxed or unbiased state. As was the case in the previous embodiments, this, in turn, causes the spring fingers 88, 90 to come together and block the needle tip 26. In this embodiment, the needle is blocked both by the spring clip as well as the shroud. As readily understood by a person of ordinary skill in the art, although the shroud 112 covers the needle tip 26 at the end of the needle withdrawal operation, it can be moved in the proximal direction off the needle tip if desired.

In all of the above described embodiments, each safety spring clip 20, 84, 110 provided in accordance with the practice of the present invention operates to block the needle tip 26 and be secured to the needle via two separate mechanisms. In a first mechanism, the spring fingers 46, 88 on the safety spring clip 20, 84, 110 are configured to move over needle tip 26 thereby blocking the needle tip and preventing movement of the spring clip in the proximal direction on the needle. In the second mechanism, the restraining opening 78 in the end wall 58, 87 is configured to interact with the needle stop 50 so that the spring clip is prevented from being moved off the needle in the distal direction.

Although three illustrative embodiments of the safety spring clip 20 are shown in FIGS. 1a to 3e and discussed above, any suitable safety spring clip design can be utilized in the present invention provided that the spring clip functions to block the needle tip 26 and cannot be accidentally disengaged from the needle tip once engaged. The spring clips 20, 84, 110 disclosed herein are preferably made of an integral construction and from stainless steel or other suitable material with the necessary memory characteristics and spring constant.

Regardless of the specific embodiment utilized, as the catheter assembly is introduced into a patient's vein and needle is withdrawn, the needle tip 26 is automatically blocked by the safety spring clip upon complete separation from the catheter hub. The needle tip 26 is therefore passively blocked by the sliding action of the needle out from the implanted catheter. In other words, a separate step or action to specifically activate the safety spring clip is not required. Accordingly, the user is not required to perform any operations outside of those currently employed when using conventional needle catheter introducers. The combined actions of the spring clip, spring arms, and the needle stop allows the safety spring clip to automatically engage and block the tip of the needle once the catheter insertion procedure is completed (i.e., once the needle assembly is fully retracted). During operation, there is only minimal frictional engagement or no adverse friction between the safety spring clip, the needle shaft, and the needle hub.

Referring now to FIGS. 4a and 4b, there is shown the catheter assembly as described with respect to the embodiment of FIGS. 1a and 1b, but with the Luer fitting 70 modified to include a fitting 133. The fitting 133 comprises a pair of threads 132 which are interrupted by a pair of generally flat surfaces or flats 143. Indented into the flats 143 are a pair of slots or indentations 137. The slots 137 are shown aligned perpendicular to the wings 56 in FIG. 4b, which is an end view taken at line D-D of FIG. 4a. The slots 137 are configured to receive the spring lips 48 and act as a gripping point for the safety spring clip 20 in a similar manner as the Luer fitting 70 in FIG. 1b.

In an exemplary embodiment, the needle hub 14 is attached to the catheter hub 15 by first inserting the needle 12 into the concentric bore of the catheter 16 and then concurrently aligning the spring lips 48 (on the safety spring clip 20) with the slots 137 on the catheter hub and continuing to insert the needle until the proximal end of the catheter hub 15 and the distal end of the needle hub 14 abut one another.

As readily understood by a person of ordinary skill in the art, the needle hub 14 and the catheter hub 15 can be configured so that they mate in a pre-determined fashion. In other words, it is possible to have a ready position whereby the wings 56 are aligned with certain stamp or label or design on the needle hub 14. In an exemplary embodiment, this may be accomplished by configuring the slots 137 and the threads 132 to engage the safety spring clip 20 in such a way that when the catheter hub 15 and the needle hub 14 are mated in the ready position, the desired appearance/configuration is achieved. In the embodiment shown in FIG. 4a, the catheter hub 15 and the needle hub 14 are configured so that the spring distal end walls 46 are in a plane substantially parallel to the wings 56 on the catheter hub.

Although the preferred embodiments of the invention have been described with some specificity, the description and drawings set forth herein are not intended to be delimiting, and persons of ordinary skill in the art will understand that various modifications may be made to the embodiments discussed herein without departing from the scope of the invention, and all such changes and modifications are intended to be encompassed within the appended claims. Various changes to the catheter introducer assembly may be made including manufacturing the dimensions differently, using different materials, changing the order of separation between the different components, and adding or changing the slots/slits including eliminating the slots/slits, the frictional force, changing the angle of the bumps, etc. Accordingly, many alterations and modifications may be made by those having ordinary skill in the art without deviating from the spirit and scope of the invention.

What is claimed is:

1. An IV catheter assembly comprising:
    a catheter hub comprising a catheter tube attached thereto and extending therefrom, said catheter tube defining a longitudinal axis;
    a shroud housing comprising a wall surface defining a cavity and having a safety clip loosely positioned therein such that it is movable relative to the shroud housing, and separated from the shroud housing when in a used position; the shroud housing comprising a distal portion and a proximal portion, said distal portion being generally cylindrical and overlaps with a portion of the catheter hub and said shroud housing being separable from the catheter hub;
    a needle hub comprising a wall surface defining a flash chamber and having a needle comprising a needle tip attached thereto; said needle extending distally of the needle hub and projecting through the shroud housing, an opening on a proximal wall of the safety clip, the catheter hub, and the catheter tube; said needle hub further comprising a distally extending wall surface defining a holding bore and having at least a portion of the shroud housing positioned therein; and
    wherein the safety clip comprises at least one arm comprising a distal wall comprising a curved lip, said curved lip being radially biased against a side of the needle, and wherein the at least one arm is resilient and flexes over the needle tip when the catheter assembly is in the used position.

2. The catheter assembly of claim 1, wherein the catheter hub comprises a Luer thread.

3. The catheter assembly of claim 1, wherein the needle comprises a needle stop comprising an enlarged diameter section adjacent a nominal needle diameter section.

4. The catheter assembly of claim 1, wherein the curved lip of the at least one arm comprises a portion that points proximally towards the needle hub.

5. The catheter assembly of claim 1, wherein the safety clip comprises a second arm extending distally of the proximal wall and crossing the needle when in a ready to use position.

6. The catheter assembly of claim 1, wherein the safety clip is made of a metallic material.

7. The catheter assembly of claim 1, wherein the proximal wall, the at least one arm, and the distal wall of the safety clip are integrally formed.

8. The catheter assembly of claim 1, wherein the holding bore is bounded by two spaced apart axially extending wall members.

9. An IV catheter assembly comprising:

a catheter hub comprising a catheter tube attached thereto and extending therefrom, said catheter tube defining a longitudinal axis;

a shroud housing comprising a wall surface defining a cavity and having a safety clip positioned therein and completely surrounded radially by the wall surface; the shroud housing comprising a distal portion and a proximal portion, said distal portion being generally cylindrical and overlaps with a portion of the catheter hub;

a needle hub comprising a wall surface defining a flash chamber and having a needle comprising a needle tip attached thereto; said needle extending distally of the needle hub and projecting through the shroud housing, an opening on a proximal wall of the safety clip, the catheter hub, and the catheter tube; said needle hub further comprising a holding bore receiving at least a portion of the shroud housing therein; and wherein the safety clip comprises at least one arm comprising a distal wall comprising a curved lip, said curved lip being radially biased against a side of the needle, wherein the safety clip is separated from the shroud housing when in a used position.

10. The catheter assembly of claim 9, wherein the catheter hub comprises a Luer thread.

11. The catheter assembly of claim 9, wherein the needle comprises a needle stop comprising an enlarged diameter section adjacent a nominal needle diameter section.

12. The catheter assembly of claim 11, wherein the needle stop is configured to engage the opening of the proximal wall when the catheter assembly is in a used position.

13. The catheter assembly of claim 9, wherein the safety clip comprises a second arm extending distally of the proximal wall and crossing the needle when in a ready to use position.

14. The catheter assembly of claim 9, wherein the safety clip is made of a metallic material.

15. The catheter assembly of claim 9, wherein the proximal wall, the at least one arm, and the distal wall of the safety clip are integrally formed.

16. The catheter assembly of claim 9, wherein the holding bore is bounded by two spaced apart axially extending wall members.

17. An IV catheter assembly comprising:

a catheter hub comprising a catheter tube attached thereto and extending therefrom, said catheter tube defining a longitudinal axis;

a shroud housing comprising a wall surface defining a cavity and having a safety clip loosely positioned therein and surrounded radially by the wall surface; the shroud housing comprising a distal portion and a proximal portion, said distal portion being generally cylindrical and overlaps with a portion of the catheter hub;

a needle hub comprising a wall surface defining a flash chamber and having a needle comprising a needle stop of an enlarged diameter relative to a nominal needle diameter located proximal of a needle tip; said needle extending distally of the needle hub and projecting through the shroud housing, an opening on a proximal wall of the safety clip, the catheter hub, and the catheter tube; said needle hub further comprising a holding bore receiving at least a portion of the shroud housing therein; and wherein the safety clip comprises at least one arm comprising a distal wall comprising a curved lip, said curved lip being radially biased against a side of the needle and said opening on said proximal wall configured to engage said needle stop in a used position, and wherein the safety clip is separated from the shroud housing and the at least one arm is resilient and flexes over the needle tip when the catheter assembly is in the used position.

18. The catheter assembly of claim 17, wherein the safety clip comprises a second arm extending distally of the proximal wall and crossing the needle when in a ready to use position.

19. The catheter assembly of claim 17, wherein the proximal wall, the at least one arm, and the distal wall of the safety clip are integrally formed.

20. The catheter assembly of claim 17, wherein the holding bore is bounded by two spaced apart axially extending wall members.

* * * * *